US010231925B2

(12) United States Patent
Heep et al.

(10) Patent No.: US 10,231,925 B2
(45) Date of Patent: Mar. 19, 2019

(54) PHARMACEUTICALS CONTAINING FLUOROQUINOLONES

(75) Inventors: Iris Heep, Köln (DE); Kristine Fraatz, Burscheid (DE); Hans-Jürgen Hamann, Dormagen (DE); Markus Edingloh, Leverkusen (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 1141 days.

(21) Appl. No.: 12/280,448

(22) PCT Filed: Feb. 23, 2007

(86) PCT No.: PCT/EP2007/001569
§ 371 (c)(1),
(2), (4) Date: Sep. 29, 2009

(87) PCT Pub. No.: WO2008/025380
PCT Pub. Date: Mar. 6, 2008

(65) Prior Publication Data
US 2010/0009979 A1    Jan. 14, 2010

(30) Foreign Application Priority Data
Mar. 8, 2006   (DE) .................. 10 2006 010 643

(51) Int. Cl.
A61K 9/00      (2006.01)
A61K 47/02     (2006.01)
A61K 47/18     (2017.01)
A61K 31/47     (2006.01)

(52) U.S. Cl.
CPC ............ *A61K 9/0019* (2013.01); *A61K 47/02* (2013.01); *A61K 47/186* (2013.01); *A61K 31/47* (2013.01)

(58) Field of Classification Search
CPC .... A61K 47/02; A61K 47/186; A61K 9/0019; A61K 31/4725; A61K 47/22; A61K 31/4709; A61K 31/47
USPC .......................................... 514/300; 546/113
See application file for complete search history.

(56) References Cited

U.S. PATENT DOCUMENTS

| | | | |
|---|---|---|---|
| 4,551,456 A * | 11/1985 | Katz .................. | 514/253.08 |
| 4,973,590 A | 11/1990 | Preiss et al. | |
| 5,225,413 A | 7/1993 | Naik et al. | |
| 5,304,559 A | 4/1994 | Rozier | |
| 5,334,589 A | 8/1994 | Al-Razzak et al. | |
| 5,679,336 A | 10/1997 | Ali et al. | |
| 5,811,130 A | 9/1998 | Boettner et al. | |
| 6,278,013 B1 * | 8/2001 | Bartel et al. ............ | 558/415 |
| 6,284,804 B1 | 9/2001 | Singh et al. | |
| 6,482,799 B1 | 11/2002 | Tuse et al. | |
| 6,492,336 B1 | 12/2002 | Mahiout | |
| 6,605,295 B1 | 8/2003 | Bellman et al. | |
| 6,605,751 B1 | 8/2003 | Gibbins et al. | |
| 6,916,484 B1 | 7/2005 | Kuhn et al. | |
| 2002/0049192 A1 | 4/2002 | Ledoussal et al. | |
| 2006/0034926 A1 | 2/2006 | Fraatz et al. | |
| 2006/0122159 A1 * | 6/2006 | Huq ................... | A61K 31/4174 514/171 |
| 2007/0082911 A1 | 4/2007 | Daube et al. | |

FOREIGN PATENT DOCUMENTS

| | | |
|---|---|---|
| RU | 2248199 C1 | 3/2005 |
| WO | 9109616 A1 | 7/1991 |
| WO | 9818492 | 5/1998 |
| WO | 9929322 A | 6/1999 |
| WO | 0064429 A | 11/2000 |
| WO | 0122936 A1 | 4/2001 |
| WO | WO 2004087043 A2 * | 10/2004 |

OTHER PUBLICATIONS

Pijls et. al., European Journal of Pharmaceutics and Biopharmaceutics, 2005, Elsevier, vol. 59, pp. 283-288.*
Stedman's medical dictionary, 2000, Lippincott, Williams and Wilkins, $27^{th}$ ed.*
Hooper, The Lancet Infectious Diseases, 2002, The Lancet Publishing Group, vol. 2, pp. 530-538.*
Chen et al., X-Ray Crystal Structures of MG2+ and CA2+ Dimers of the Antibacterial Drug Norfloxacin; J. Chem. Soc., Dalton Trans., 2000, pp. 4013-4014.
Campbell et al., Norfloxacin Interaction With Antacids and Minerals; BR. J. Clin. Pharmac., 1992, No. 33, pp. 115-116.
Wallis et al., Interaction of Norfloxacin With Divalent and Trivalent Pharmaceutical Cations, In Vitro Complexation and In Vivo Pharmacokinetic Studies in the Dog; Journal of Pharmaceutical Sciences. Aug. 1996, vol. 85. No. 8, pp. 803-809.
Niazi, S.K., Handbook of Pharmaceutical Manufacturing Formulations; CRC Press LLC, 2004, vol. 6, Part II, pp. 1-6.
Song et al., A Fluorescence Spectroscopic Study of the Interaction Between Norfloxacin and DNA; Canadian Journal of Analytical Sciences and Spectroscopy, 2004, vol. 49, No. 4, pp. 203-209.
Cheshuev, V.I., "Promyshlennaia Tekhnologia Lekarstvennyh Sredstv" (=Large-Scale Technology of Drugs); Kharkov, HRGB. "Osnova", 1999, vol. 2, pp. 574-575.
Bas, et al., "Efficacies of free and liposome-encapsulated enrofloxacin (Baytril®) against *Staphylococcus aureus* infection in Turkish Shepherd Dog neutrophils in vitro," Revue Med. Vet. 2000, 151(5):415-420.

(Continued)

*Primary Examiner* — Sarah Pihonak
(74) *Attorney, Agent, or Firm* — McBee Moore Woodward & Vanik IP, LLC

(57) ABSTRACT

The invention relates to the use of quaternary ammonium compounds for preventing precipitations of fluoroquinolones from their solutions and to stable, tolerated pharmaceuticals which are particularly suitable for parenteral use and which contain, in dissolved form, a fluoroquinolone and a quaternary ammonium compound.

23 Claims, No Drawings

(56) References Cited

OTHER PUBLICATIONS

Fang, J-Y et al., "Characterization and Stability of Various Liposome-Encapsulated Enoxacin Formulations," Chem. Pharm Bulletin, 1997, 45(( ):1504-1997.
Kovoor et al., "Evaluation of the corneal effects of topical ophthalmic fluoroquinolones using in vivo confocal microscopy.," Eye & Contact Lens, Apr. 2004, 30(2):90-4.
PCT International Search Report dated Jul. 16, 2007, 6 pgs.

* cited by examiner

PHARMACEUTICALS CONTAINING FLUOROQUINOLONES

The invention relates to the use of quaternary ammonium compounds for preventing precipitations of fluoroquinolones from their solutions and to stable, tolerated pharmaceuticals which are particularly suitable for parenteral use and which contain, in dissolved form, a fluoroquinolone and a quaternary ammonium compound.

Extensive research has been carried out in the field of the solubilization of antibiotically active fluoroquinolones. Thus, DE-OS-3 831 514 describes solutions with quinolones by using metal ions, in particular calcium ions. An improved solubility of quinolones is also described in JP 02-264724 and by M. Nakano, M. Yamamoto, T. Arita in Chem. Pharm. Bull., Interactions of Aluminium, Magnesium and Calcium ions with Nalidixic acid, 26 (5) 1505-1510 (1978) by using metal ions, in particular magnesium ions. EP-A 507 851 describes complexes of quinolones with metal ions and acid; the solubility of the quinolones is said to be improved in these complexes. The improved solubility of a fluoroquinolone by addition of metal ions and cosolvents is stated in U.S. Pat. No. 5,811,130. The tolerance of these complexes is shown in calves. Complexes of quinolones with metal ions and, specifically, with magnesium ions are also described in WO 99/29322, the intention being to achieve a better solubility of the quinolones. The complexes described therein are described as being well tolerated and storage-stable, the tolerance in calves and rats having been studied.

Solutions for pharmaceutical purposes must be free of precipitations. This is particularly important in solutions for parenteral administration, and even a small extent of precipitations, referred to as particle formation, is not acceptable. This applies over the entire shelf life of a product which is used for pharmaceutical purposes. There therefore exists a large number of publications on the subject of avoiding particle formation or precipitation of pharmaceutical agents from solutions. For example, WO 98/18492 describes that the formation of particles in solutions with cephalosporins is avoided by using phospholipids.

EP-A 287 926 describes a detailed purification method specifically for the synthesis of fluoroquinolones to avoid particle formation when preparing solutions (for injection). Likewise, WO 01/10408 describes that materials with a particularly low degree of metal ion contamination must be used for the preparation of fluoroquinolone solutions for injection to ensure that the solutions remain free of particles.

An equally frequently chosen way of avoiding the problem of particle formation is, for example, the freeze-drying of solutions.

It is generally known that surface-active substances are not well tolerated on parenteral administration. This can be attributed inter alia to the affinity of the surface-active substances with cell wall constituents. Surface-active substances with a particularly pronounced affinity for cell walls are therefore also employed inter alia as disinfectants or as preservatives. This also applies to preservatives from the group of the quaternary ammonium compounds such as, for example, benzalkonium chloride.

It is also generally known that the group of the quaternary ammonium compounds are irritants of the skin and the mucosa. Thus, K. H. Wallhäuser (in Praxis der Sterilisation, Desinfektion-Konservierung, Thieme Verlag, 1995, 5th edition, pp. 586-598) describes the skin-irritant effect of benzalkonium chloride on the healthy skin of rabbits; the development of various types of dermatitis in mice is also described (J. Amer. Vet. Med. Ass., 1972, 161 (6), 652-655. Dermatitis and death in mice accidentally exposed to quaternary ammonium disinfectants). In J. Gen. Microbiol., 1967, 48 (3), 391-400 ("Effects of organic cations on the gram-negative cell wall and their bactericidal activity with EDTA and surface active agents"), the mechanism of the action of quaternary ammonium compounds is shown, with the interaction with the cell membranes and the resulting increase in the permeability for other substances being described explicitly.

While the improvement of the solubility of fluoroquinolones by adding metal ions such as, for example, magnesium ions or calcium ions has been described in the literature in principle, the storage of some solutions of fluoroquinolones still entails the known precipitations in the form of particle formation. This also takes place when the generally customary substances for avoiding precipitations or crystallizations are being used. Thus, for example, employing the cosolvents described in U.S. Pat. No. 5,811,130 or acid-containing formulations as described in EP-A 507 851 does not prevent particle formation in pradofloxacin solutions.

Moreover, formulations of the fluoroquinolones are not equally well tolerated by various animal species so that a tolerance which has been determined in calves does not allow the conclusion that a tolerance in, for example, pigs or dogs or indeed cats can be assumed. This is also true for the opposite case: solutions for injection which are tolerated by dogs are not necessarily tolerated by cats or calves.

In contrast to the livestock sector (for example cattle), the assessment of the local tolerance of solutions for injection is, besides the objective local findings, is more critical in pets (for example dogs or cats). Thus, the animal owners' acceptance of minor local intolerances (for example swellings, pain) is markedly lower in the pet sector than in the livestock sector. In addition, the breed variants found in the pet sector in particular frequently react more sensitively to subcutaneous injections compared with livestock. In this context, cats must be mentioned as highly sensitive animal species. It is therefore not surprising that most of the fluoroquinolone solutions for injection are not available for dogs or cats as the result of, inter alia, lacking tolerance.

To create the best possible tolerance, it is recommended to keep the pH of the solutions as neutral as possible (approx. 7.4), which, however, is in contrast to the solubility of the fluoroquinolones, since the latter are, as a rule, particularly sparingly soluble at neutral pH. This applies in particular to the aqueous systems which are preferably used for quinolones, where, as a result of the poor solubility of the quinolones at pH values around neutral, additives such as cosolvents must be used. Particle formation of the betaine form of the fluoroquinolones can be observed frequently in the neutral pH range, which is why solutions, while being tolerated, are frequently not storage-stable, and particle formation results. In practice, this phenomenon is frequently circumvented for example by using freeze-dried products. However, freeze-dried products are complicated to handle in practice, and, as a rule, the reconstituted solution has a short shelf life (for example 4 weeks) after reconstitution, or must be discarded directly as the result of the possibility of particle formation. Thus, such products have pronounced disadvantages over a ready-to-use solution for injection which can be administered directly.

Accordingly a ready-to-use solution as solution for injection is advantageous. Furthermore, it is necessary that, following administration, as also described in WO 99/29322, a suitable amount of the fluoroquinolone enters into the serum. Again, this is not a matter of course in the case of fluoroquinolone formulations for injection, and may also depend on the animal species in question.

A possibility of reliably keeping fluoroquinolones in solution has been found, using pharmaceutically acceptable additives. Thus, ready-to-use formulations with fluoroquinolones can be provided which contain a sufficient concentration of the fluoroquinolone, which are well tolerated locally by various animal species following parenteral administration, which are stable under pharmaceutical storage conditions, which are free of particle formation, and which have an advantageous profile in terms of serum kinetics.

The invention relates to:
the use of quaternary ammonium compounds for preventing precipitations of fluoroquinolones from their solutions.

The invention furthermore relates to:
a pharmaceutical containing, in dissolved form:
(a) a fluoroquinolone, if appropriate in the form of a pharmaceutically useful salt and
(b) a quaternary ammonium compound.

Fluoroquinolones are compounds as they are disclosed, inter alia, in the following documents: U.S. Pat. No. 4,670,444 (Bayer AG), U.S. Pat. No. 4,472,405 (Riker Labs), U.S. Pat. No. 4,730,000 (Abbott), U.S. Pat. No. 4,861,779 (Pfizer), U.S. Pat. No. 4,382,892 (Daiichi), U.S. Pat. No. 4,704,459 (Toyama), the following being mentioned as specific examples: benofloxacin, binfloxacin, cinoxacin, ciprofloxacin, danofloxacin, difloxacin, enoxacin, enrofloxacin, fleroxacin, ibafloxacin, levofloxacin, lomefloxacin, marbofloxacin, moxifloxacin, norfloxacin, ofloxacin, orbifloxacin, pefloxacin, temafloxacin, tosufloxacin, sarafloxacin, sparfloxacin.

A preferred group of fluoroquinolones are those of the formula (I) or (II):

(I)

(II)

in which
X represents hydrogen, halogen, $C_{1-4}$-alkyl, $C_{1-4}$-alkoxy, $NH_2$,
Y represents radicals of the structures in which
$R^4$ represents optionally hydroxyl- or methoxy-substituted straight-chain or branched $C_1$-$C_4$-alkyl, cyclopropyl, acyl having 1 to 3 C atoms,
$R^5$ represents hydrogen, methyl, phenyl, thienyl or pyridyl,
$R^6$ represents hydrogen or $C_{1-4}$-alkyl,
$R^7$ represents hydrogen or $C_{1-4}$-alkyl,
$R^8$ represents hydrogen or $C_{1-4}$-alkyl,
and
$R^1$ represents an alkyl radical having 1 to 3 carbon atoms, cyclopropyl, 2-fluoroethyl, methoxy, 4-fluorophenyl, 2,4-difluorophenyl or methylamino,
$R^2$ represents hydrogen or optionally methoxy- or 2-methoxyethoxy-substituted alkyl having 1 to 6 carbon atoms and cyclohexyl, benzyl, 2-oxopropyl, phenacyl, ethoxycarbonylmethyl, pivaloyloxymethyl,
$R^3$ represents hydrogen, methyl or ethyl and
A represents nitrogen, =CH—, =C(halogen)-, =C(OCH$_3$)—, =C(CH$_3$)— or =C(CN),
B represents oxygen, optionally methyl- or phenyl-substituted =NH or =CH$_2$,
Z represents =CH— or =N—,
and their pharmaceutically useful salts and hydrates.

Preferred compounds of the formula (I) are those
in which
A represents =CH— or =C—CN,
$R^1$ represents optionally halogen-substituted $C_1$-$C_3$-alkyl or cyclopropyl,
$R^2$ represents hydrogen or $C_{1-4}$-alkyl,
Y represents radicals of the structures in which
$R^4$ represents optionally hydroxyl-substituted straight-chain or branched $C_1$-$C_3$-alkyl, oxalkyl having 1 to 4 C atoms,
$R^5$ represents hydrogen, methyl or phenyl,
$R^6$ represents hydrogen or methyl,
$R^7$ represents hydrogen or methyl,
$R^8$ represents hydrogen or methyl,
and their pharmaceutically useful hydrates and salts.

Especially preferred compounds of the formula (I) are those
in which
A represents =CH— or =C—CN,
$R^1$ represents cyclopropyl,
$R^2$ represents hydrogen, methyl or ethyl,
Y represents radicals of the structures

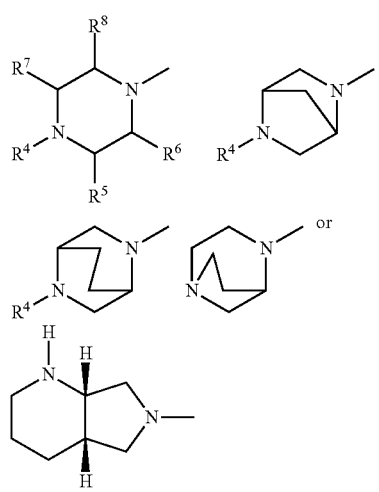

in which
$R^4$ represents methyl, optionally hydroxyl-substituted ethyl,
$R^5$ represents hydrogen or methyl,
$R^6$ represents hydrogen,
$R^7$ represents hydrogen or methyl,
$R^8$ represents hydrogen,
and their pharmaceutically useful salts and hydrates.

A preferred example of a fluoroquinolone of the formula (II) which may be mentioned is marbofloxacin:

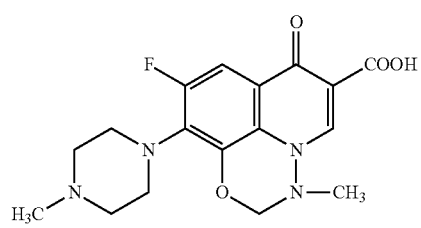

Especially preferred fluoroquinolones which may be mentioned are the compounds described in WO 97/31001, in particular 8-cyano-1-cyclopropyl-7-((1S,6S)-2,8-diazabicyclo[4.3.0]nonan-8-yl)-6-fluoro-1,4-dihydro-4-oxo-3-quinolinecarboxylic acid (pradofloxacin), of the formula

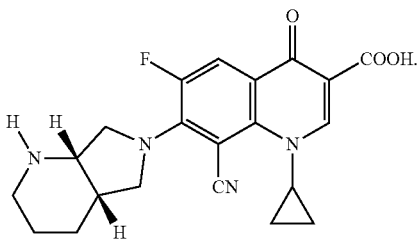 [SMILES: N#Cc1c(N2C[C@@H]3CCCN[C@@H]3C2)c(F)cc2c(=O)c(C(=O)O)cn(C3CC3)c12]

Enrofloxacin is also especially preferably employed: 1-cyclopropyl-7-(4-ethyl-1-piperazinyl)-6-fluoro-1,4-dihydro-4-oxo-3-quinolinecarboxylic acid

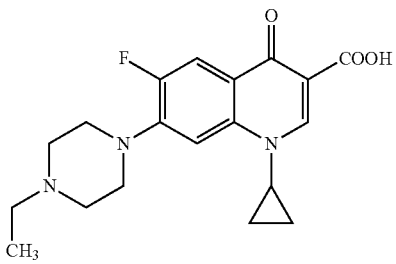 [SMILES: CCN1CCN(c2cc3c(cc2F)c(=O)c(C(=O)O)cn3C2CC2)CC1]

The use of ciprofloxacin, an active substance usually employed in human medicine, is also feasible.

The fluoroquinolones can exist in the form of their racemates or in enantiomeric forms. Not only the pure enantiomers, but also their mixtures can be employed in accordance with the invention.

Suitable salts are pharmaceutically useful acid addition salts and basic salts.

Pharmaceutically useful salts are taken to mean, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid. Furthermore, the compounds according to the invention can be bound to acidic or basic ion exchangers. Pharmaceutically useful basic salts which may be mentioned are the alkali metal salts, for example the sodium or potassium salts, the alkaline earth metal salts, for example the magnesium or calcium salts; the zinc salts, the silver salts and the guanidinium salts.

Hydrates are taken to mean not only the hydrates of the fluoroquinolones themselves, but also the hydrates of their salts. An example which may be mentioned is pradofloxacin, which forms a stable trihydrate (see WO 2005/097789).

Fluoroquinolones, being solids, can, under certain circumstances, form various crystal modifications. Advantageous for the pharmaceuticals of the present invention are those modifications which have suitable solubility properties.

In the pharmaceuticals according to the invention, the fluoroquinolone is employed in animals with a body weight of up to approximately 80 kg, typically in an amount of 0.1 to 15%, preferably 0.5 to 15% and especially preferably 1 to 15%. In the case of animals with a body weight of more than approximately 80 kg, the fluoroquinolone is typically employed in an amount of from 1 to 30%, preferably 3 to 25% and especially preferably 4 to 20%. Unless otherwise specified, the percentages are understood as meaning percent (w/v) here and hereinbelow. This means: weight of the substance in question in grams per 100 ml of finished solution.

The pharmaceuticals according to the invention may contain further suitable active substances such as, for example, analgesics, in particular NSAIDs (nonsteroidal anti-inflammatory substances). Examples of such NSAIDs can be: meloxicam, flunixin, ketoprofen, carprofen, metamizole or (acetyl-)salicylic acid.

Quaternary ammonium compounds for the purposes of the present invention are usually organic ammonium compounds which have unpolar substituents and which may have a variety of counterions such as, for example, chloride, bromide, iodide or fluoride. They are preferably compounds of the general formula (III):

$$[R^1R^2R^3R^4N]^+X^-  \quad (III)$$

where $R^1$ to $R^4$ are identical or different and represent $C_{1-18}$-alkyl which can optionally be interrupted once or more than once by oxygen and which can optionally be substituted by hydroxyl or by an aryl radical which is optionally substituted by one or more halogen atoms or $C_{1-8}$-alkyl radicals, or $R^1$ to $R^4$ may, as the result of the cyclization of three radicals, form 5- or 6-membered heterocyclic radicals such as, for example, pyridine or thiazoline, which, in turn, are optionally mono- or polysubstituted by $C_{1-4}$-alkyl or $C_{1-4}$-alkenyl, which optionally have attached to them an aryl radical which, in turn, can be substituted by halogen, in particular chlorine, amino or dimethylamino, and X represents sulphate, halide, in particular chloride, bromide or iodide, or a similar counterion.

At least one of the radicals $R^1$ to $R^4$ preferably has a chain length of 8 to 18, especially preferably 12 to 16, C atoms.

Aryl preferably represents a phenyl radical which is optionally substituted by 1 or 2 radicals selected among halogen, in particular chlorine, and $C_{1-8}$-alkyl.

Examples are alkyldimethylbenzylammonium chlorides, in particular benzalkonium chloride [($C_{8-18}$)-alkyldimethylbenzylammonium chloride] or n-($C_{12}$-$C_{18}$)-alkylbenzyldimethylammonium chloride with average molecular weights of approximately 380, benzethonium chloride (diisobutylphenoxyethoxyethyldimethylbenzylammonium chloride), dichlorobenzyldimethylalkylammonium chloride, benzoxonium chloride (benzyldodecylbis(2-hydroxyethyl)ammonium chloride), cetrimonium bromide (N-hexadecyl-N,N-trimethylammonium bromide, di-($C_8$-$C_{18}$)-alkyldimethylammonium chloride such as, for example, dioctyldimethylammonium chloride or di-n-decyldimethylammonium chloride, cetylpyridinium chloride (1-hexadecylpyridinium chloride) and thiazoline iodide (3-heptyl-2-(3-heptyl-4-methyl-4-thiazolin-2-ylidenemethyl)-4-methylthiazolinium iodide). Especially preferred among these are benzethonium chloride and benzalkonium chloride.

The quaternary ammonium compounds are usually employed in concentrations of from 0.001 to 10%, preferably from 0.005 to 6% and especially preferably from 0.005 to 3%. The percentages mean % (w/v).

In addition to the quaternary ammonium compounds, the medicaments according to the invention can additionally contain further substances which can avoid particle formation; for example poloxamers, lecithins, polyvinylpyrrolidones, cosolvents, antioxidants or complexing agents. Again, these are usually employed in concentrations of 0.001 to 20%, preferably 0.01 to 10% and especially preferably 0.05 to 3%. The percentages mean % (w/v).

The liquid formulations can contain substances which improve the local tolerance upon application. Examples which may be mentioned are: free-radical scavengers or antioxidants such as, for example, vitamin E, water-soluble vitamin E esters or vitamin C, butylhydroxyanisole, butylhydroxytoluene, cysteamine, cysteine, glutathione, thioglycol, thiolactic acid, sodium disulphide or else acetylcysteine. Complexing agents such as, for example cyclodextrins (for example hydroxypropylcyclodextrin), sodium-EDTA (ethylenediaminetetraacetic acid), polyvinylpyrrolidone, dexpanthenol, salts of fatty acids such as, for example, sodium caprylate, salts of polyvalent metal cations (for example $Me^{2+}$ or $Me^{3+}$), in particular of the alkaline earth metals and here in particular magnesium in its salt forms, amino acids and here particularly arginine or lysine, poloxamers, poloxamines, cosolvents such as, for example, n-butanol, glycerol, polyethylene glycol, propylene glycol or dimethylacetamide, dextrans, creatine, creatinine, acids such as, for example, gluconolactonic acid, lactic acid, embonic acid, citric acid, tartaric acid, mucic acid or hyaluronic acid, lecithins with a phosphatidylcholine content of 70-100% from soya or chicken protein. Among the abovementioned substances, it is preferable to employ the salts of polyvalent metal cations, and here preferably the alkaline earth metal salts, in particular magnesium salts.

Substances which improve the tolerance are usually employed in concentrations of from 0.05 to 10%, preferably 0.1 to 8% and especially preferably 0.5 to 5%. The percentages mean % (w/v).

The solvent which the liquid formulation may contain is water or water-miscible substances. Examples which may be mentioned are glycerol, propylene glycol, polyethylene glycols, tolerated alcohols such as ethanol, benzyl alcohol or n-butanol, ethyl lactate, ethyl acetate, triacetin, N-methylpyrrolidone, propylene carbonate, glycofurol, dimethylacetamide, 2-pyrrolidone, isopropylidene glycerol, or glycerin formal. Combinations of the solvents are also feasible. Waterbased formulations, which naturally may also contain further solvents and cosolvents, are preferred.

Besides water or water-miscible substances, the liquid formulation may also contain oils in the form of an emulsion as solvent. Among these, substances which may be mentioned are the vegetable, animal and synthetic oils such as cottonseed oil, sesame oil, soya oil, medium-chain triglycerides with a chain length of $C_{12}$-$C_{18}$, propylene glycol octanoate/decanoate or else paraffin.

The solvent is usually present in concentrations of up to 98.5%, preferably up to 97%, especially preferably up to 96.5%. As a rule, the solvent concentrations are above 50%, preferably above 60%, especially preferably above 70%. The percentages mean % (w/v).

The formulations according to the invention may also contain cosolvents, and here preferably in those cases when the formulations contain water; the cosolvents can improve the solubility of certain formulation constituents. The cosolvents are usually employed in amounts of from 1 to 10%, preferably 3 to 8% (percentages in each case w/v). Examples of cosolvents which may be mentioned are: pharmaceutically tolerated alcohols, dimethyl sulphoxide, ethyl lactate, ethyl acetate, triacetin, N-methylpyrrolidone, propylene carbonate, propylene glycol, glycofurol, dimethylacetamide, 2-pyrrolidone, isopropylidene glycerol, glycerine formal, glycerin and polyethylene glycols. Substances which are suitable as cosolvent are, in particular, pharmaceutically acceptable alcohols such as, for example, ethanol, benzyl alcohol or n-butanol. Mixtures of the abovementioned solvents may also be employed as cosolvent.

The liquid formulation may contain preservatives. As a rule, the abovementioned quaternary ammonium compounds have a preserving activity, for example benzalkonium chloride, benzethonium chloride or cetylpyridinium chloride. The following may be mentioned as examples of further preservatives which may be used: aliphatic alcohols such as benzyl alcohol, ethanol, n-butanol, phenol, cresols, chlorobutanol, para-hydroxybenzoic esters (in particular the methyl and propyl esters), salts or the free acids of the carboxylic acids, such as sorbic acid, benzoic acid, lactic acid or propionic acid.

Depending on the type of formulation and on the form of administration, the pharmaceuticals according to the invention may contain further customary, pharmaceutically acceptable additives and adjuvants. Examples which may be mentioned are:

antioxidants such as, for example, sulphites (Na sulphite, Na metabisulphite), organic sulphides (cystine, cysteine, cysteamine, methionine, thioglycerol, thioglycolic acid, thiolactic acid), phenols (tocopherols, and also vitamin E and vitamin-E-TPGS (d-alpha-tocopheryl polyethylene glycol 1000 succinate)), butylhydroxyanisole, butylhydroxytoluene, octyl and dodecyl gallate), organic acids (ascorbic acid, citric acid, tartaric acid, lactic acid) and their salts and esters, wetting agents such as, for example, salts of fatty acids, or fatty alkyl sulphates, fatty alkyl sulphonates, linear alkylbenzene sulphonates, fatty alkyl polyethylene glycol ether sulphates, fatty alkyl polyethylene glycol ethers, alkylphenol polyethylene glycol ethers, alkyl polyglycosides, fatty acid N-methylglucamides, polysorbates, sorbitan fatty acid esters and poloxamers.

Iso-osmotics, such as, for example, sodium chloride, glucose or glycerol.

Pharmaceutically acceptable colorants such as, for example, iron oxides, carotenoids and the like.

The pH of the liquid formulations is 2-11, preferably 3-8 and especially preferably 4-7.6.

The pharmaceuticals according to the invention can be prepared by dispersing the fluoroquinolone in the solvent and the substances for improving tolerance and, if appropriate, for avoiding particle formation are likewise added. Cosolvents and further constituents such as, for example, preservatives can already be added to the solvent or else admixed later.

Alternatively, cosolvents, preservatives, substances which influence the tolerance or the formation of particles may also first be dissolved in the solvent and the mixture is only then complemented by the fluoroquinolone.

In general, the pharmaceutical preparations according to the invention are suitable for use in humans and animals. They are preferably employed in animal keeping and animal husbandry in livestock, breeding animals, zoo animals, laboratory animals, experimental animals and pets.

The livestock and breeding animals include mammals such as, for example, cattle, horses, sheep, pigs, goats, camels, water buffaloes, donkeys, rabbits, fallow deer, reindeer, fur bearers such as, for example, minks, chinchilla, racoons and birds such as, for example, quails, chickens, geese, turkeys, ducks, pigeons and bird species for keeping on domestic premises and in zoos.

The laboratory and experimental animals include mice, rats, guinea pigs, golden hamsters, rabbits, monkeys, dogs and cats.

The pets include rabbits, hamsters, rats, guinea pigs, mice, horses, reptiles, suitable bird species, dogs and cats.

Fish may also be mentioned, and here useful fish, farmed fish, aquarium fish and ornamental fish of all ages which live in fresh water and sea water.

The preparations according to the invention are preferably employed in pets such as horses, rabbits, cats and dogs. They are particularly suitable for use in cats and dogs.

Examples of preferred livestock are cattle, sheep, pig, goat, turkey and chicken. Especially preferred livestock is cattle and pig.

The administration can be effected prophylactically, metaphylactically or else therapeutically.

The liquid formulations according to the invention are preferably administered as solutions or emulsions, with homogeneous solutions being especially preferred.

The formulations described herein can be administered to the target organism (human or animal) via different routes, for example, they can be administered parenterally, in particular by means of an injection (for example subcutaneously, intramuscularly, intravenously, intramammarially, intraperitoneally), dermally, orally, rectally, vaginally or nasally, with parenteral administration—in particular by means of an injection—being preferred.

The use with the abovementioned substances gives pharmaceuticals with good solubility of the active substance and good stability of the formulation, in particular with regard to precipitations. Moreover, the pharmaceutical according to the invention is also distinguished by good tolerance and suitable serum kinetics in the abovementioned various animal species, in particular upon parenteral administration.

EXAMPLES

The formulations of the following examples are prepared by mixing or dissolving the stated ingredients in water for injection. The pH of the solutions can be adjusted by addition of acids or bases. The solutions for injection are filter-sterilized and transferred into suitable containers. Pradofloxacin can be employed as the anhydrate or as the trihydrate; the numerical values are calculated in each case for the anhydrate.

(Percentages in percent by weight based on the total volume of the finished preparation, [w/v]).

Example 1

1% enrofloxacin
3.0% magnesium chloride hexahydrate
0.02% benzalkonium chloride
q.s. potassium hydroxide
water for injection to 100%

0.5 g of enrofloxacin, 1.5 g of magnesium chloride hexahydrate and 0.01 g of benzalkonium chloride are dissolved in water for injection in a final volume of 50 ml, and, if appropriate, the pH is brought to 6.0 with potassium hydroxide.

Example 2

3.0% pradofloxacin (trihydrate)
3.0% magnesium chloride hexahydrate
0.02% benzalkonium chloride
q.s. sodium hydroxide
water for injection to 100%

1.5 g of pradofloxacin (calculated as pure pradofloxacin, employed as the trihydrate), 1.5 g of magnesium chloride hexahydrate and 0.01 g of benzalkonium chloride are dissolved in water for injection at a final volume of 50 ml and, if appropriate, the pH is brought to 6.0 with sodium hydroxide.

Example 3

1.5% pradofloxacin
3% magnesium chloride hexahydrate
0.01% benzethonium chloride
water for injection to 100%

0.75 g of pradofloxacin, 1.5 g of magnesium chloride hexahydrate and 0.005 g of benzethonium chloride are dissolved in water for injection in a final volume of 50 ml, and, if appropriate, the pH is brought to 6.0 with potassium hydroxide.

Example 4

1.5% pradofloxacin (trihydrate)
3% magnesium chloride hexahydrate
0.02% benzalkonium chloride
water for injection to 100%

0.75 g of pradofloxacin (calculated as pure pradofloxacin, employed as the trihydrate), 1.5 g of magnesium chloride hexahydrate and 0.01 g of benzalkonium chloride are dissolved in water for injection at a final volume of 50 ml and, if appropriate, the pH is brought to 6.0 with sodium hydroxide.

Example 5

5% pradofloxacin (trihydrate)
0.02% benzalkonium chloride
3% magnesium chloride hexahydrate
water for injection to 100%

80 g of water for injection are mixed with 0.02 g of benzalkonium chloride and 3 g of magnesium chloride hexahydrate. 5 g of pradofloxacin (calculated as pure pradofloxacin; employed as the trihydrate) are dissolved in this mixture. The mixture is adjusted to the final weight of 100 ml with the remaining water for injection and, if appropriate, the pH is brought to 6.0 beforehand using sodium hydroxide.

Example 6

1.5% pradofloxacin (trihydrate)
0.015% benzalkonium chloride
3% magnesium chloride hexahydrate
water for injection to 100%

80 g of water for injection are mixed with 0.015 g of benzalkonium chloride and 3 g of magnesium chloride hexahydrate. 1.5 g of pradofloxacin (calculated as pure pradofloxacin; employed as the trihydrate) are dissolved in this mixture. The mixture is adjusted to the final weight of 100 ml with the remaining water for injection and, if appropriate, the pH is brought to 6.0 beforehand using sodium hydroxide.

Example 7

1.5% pradofloxacin (trihydrate)
0.01% benzalkonium chloride
3% magnesium chloride hexahydrate
water for injection to 100%

80 g of water for injection are mixed with 0.01 g of benzalkonium chloride and 3 g of magnesium chloride hexahydrate. 1.5 g of pradofloxacin (calculated as pure pradofloxacin; employed as the trihydrate) are dissolved in this mixture. The mixture is adjusted to the final weight of 100 ml with the remaining water for injection and, if appropriate, the pH is brought to 6.0 beforehand using sodium hydroxide.

In-Vivo Tolerance

In clinical trials, the formulations described herein have demonstrated an improved local tolerance in comparison with other formulations. The extent of tissue irritation and swelling at the injection site as the result of active substance depends on the formulation employed. Selected examples are listed in the table which follows.

The test system employed consists in a combined testing of local tolerance initially and over 36 days and of serum pharmacokinetics of 0-72 hours. Each formulation is tested on in each case 6 animals of the two species dog and cat following a single subcutaneous injection. The serum samples (n=11/animal) are tested for their substance concentration by means of HPLC, and the results are used to calculate the pharmacokinetic parameters. The local tolerance is assessed visually and by palpation with reference to the parameters swelling, pain, redness and skin irritation/change.

TABLE 1

Selected results of the clinical testing of various formulations for local tolerance

| Formulation | (n) | Local reactions (n) | | | | | | |
|---|---|---|---|---|---|---|---|---|
| | | initially | day 1 | day 7 | day 14 | day 21 | day 28 | day 36 |
| Cat: | | | | | | | | |
| Example 4 | 6 | 0 | 0 | 0 | 0 | 0 | 0 | 0 |
| Dog: | | | | | | | | |
| Example 2 | 9 | 0 | 0 | 0 | 0 | 0 | 0 | 0 |

(n): number of animals

Serum-Pharmacokinetic Profile

The formulation does not only affect difference in tolerance, but also the serum-pharmacokinetic (PK) profile. Different formulations differ markedly with regard to their serum concentration time-curve. Curves with rapid absorption, high peak concentrations and long elimination phases are preferred for quinolones. The table hereinbelow shows the PK profile of a formulation according to the invention. The test system used has been described in the section "local tolerance".

TABLE 2

Serum pharmacokinetics: results

| | | PK parameters (9 mg/kg, SC, dog) | | | | |
|---|---|---|---|---|---|---|
| Formulation | n | $C_{max}$ (µg/mL) | $T_{max}$ (hr) | $t_{1/2}$ (hr) | $AUC_{inf}$ (h * µg/mL) | $AUC_{last}$ (h * µg/mL) |
| Example 2 | 6 | 3.8 | 1.5 | 4.6 | 31.0 | 30.7 |

The invention claimed is:
1. A method of treating a bacterial infection in an animal comprising injecting a waterbased formulation into the animal, wherein the injectable formulation comprises i) at least 50% (w/v) water,
ii) 1 to 15% (w/v) pradofloxacin or a salt or hydrate thereof, and
iii) a quaternary ammonium compound,
wherein the waterbased formulation is a solution.

2. The method of claim 1, wherein the quaternary ammonium compound is of the general formula (III)

$$[R^1R^2R^3R^4N]^+X^- \qquad (III)$$

where
R$^1$ to R$^4$ are identical or different and represent C$_{1-18}$-alkyl which can optionally be interrupted once or more than once by oxygen and which can optionally be substituted by hydroxyl or by an aryl radical which is optionally substituted by one or more halogen atoms or C$_{1-8}$-alkyl radicals, or
R$^1$ to R$^4$ may, as the result of the cyclization of three radicals, form 5- or 6-membered heterocyclic radicals optionally mono- or polysubstituted by C$_{1-4}$-alkyl or C$_{1-4}$-alkenyl, which optionally have attached to them an aryl radical optionally substituted by halogen, amino or dimethylamino, and
X is selected from the group consisting of a sulphate and halide.

3. The method of claim 1, wherein the quaternary ammonium compound is selected from the group consisting of benzalkonium chloride, n-(C$_{12}$-C$_{18}$)-alkylbenzyldimethylammonium chloride with an average molecular weight of approximately 380, benzethonium chloride, dichlorobenzyldimethylalkylammonium chloride, benzoxonium chloride, cetrimonium bromide, dioctyldimethylammonium chloride, di-n-decyldimethylammonium chloride, cetylpyridinium chloride, and thiazoline iodide.

4. The method of claim 1 wherein the formulation comprises a single dose of pradofloxacin.

5. The method of claim 1 wherein the pH of the formulation is 4 to 7.6.

6. The method of claim 1 wherein the formulation comprises 0.005 to 3.0% (w/v) of the quaternary ammonium compound.

7. The method of claim 1 wherein the formulation further comprises at least one antioxidant, wetting agent, osmolarity agent, colorant, preservative, co-solvent, poloxamers, lecithin, polyvinylpyrrolidone, or complexing agent.

8. The method of claim 1 wherein the formulation is injected into the animal subcutaneously, intramuscularly, intravenously, intramammarially, or intraperitoneally.

9. The method of claim 1 wherein the animal treated is a livestock animal, a breeding animal, a zoo animal, a laboratory animal, an experimental animal, or a pet animal.

10. The method of claim 9 wherein the animal treated is a pet animal which is a horse, a rabbit, a cat, or a dog.

11. The method of claim 1 wherein the pradofloxacin is in enantiomeric form.

12. The method of claim 1, wherein the formulation comprises at least 70% (w/v) water.

13. The method of claim 1, wherein the quaternary ammonium compound is selected from benzalkonium chloride and benzethonium chloride.

14. The method of claim 1, wherein the formulation further comprises from 1% to 10% (w/v) of a cosolvent selected from pharmaceutically tolerated alcohols, dimethyl sulphoxide, ethyl lactate, ethyl acetate, triacetin, N-methylpyrrolidone, propylene carbonate, propylene glycol, glycofurol, dimethylacetamide, 2-pyrrolidone, isopropylidene glycerol, glycerine formal, glycerin, polyethylene glycols, and mixtures thereof.

15. The method of claim 14, wherein the cosolvent is a pharmaceutically tolerated alcohol.

16. The method of claim 15, wherein the pharmaceutically tolerated alcohol is selected from ethanol, benzyl alcohol, and n-butanol.

17. The method according to claim 1, wherein the injectable formulation is stable under pharmaceutical storage conditions and free of particle formation.

18. The method according to claim 1, wherein the animal is a cat or dog and the injectable formulation is tolerated locally by cat or dog following parenteral administration.

19. The method according to claim 1, wherein the injectable formulation has a serum-pharmacokinetic profile of $C_{max}$ of at least 3.8 µg/mL, $T_{max}$ of at least 1.5 hours, $t_{1/2}$ of at least 4.6 hours, $AUC_{inf}$ of at least 31.0 h*µg/mL, and $AUC_{last}$ of at least 30.7 h*µg/mL.

20. A method of treating a bacterial infection in an animal comprising of injecting a waterbased formulation into the animal, the injectable formulation consisting of:
at least 50% (w/v) water, 1 to 15% (w/v) pradofloxacin or a salt or hydrate thereof,
a quaternary ammonium compound, and
optionally one or more of: an antioxidant, a wetting agent, an osmolarity agent, a colorant, a preservative, a co-solvent, a poloxamer, a lecithin, a polyvinylpyrrolidone, or a complexing agent,
wherein the injectable waterbased formulation is a solution and is stable under pharmaceutical storage conditions and free of particle formation.

21. The method of claim 1, wherein pradofloxacin is the only antibiotically active substance present in the formulation.

22. The method of claim 21, wherein the quaternary ammonium compound is benzalkonium chloride.

23. An injectable formulation comprising i) at least 50% (w/v) water, ii) 1-15% (w/v) an antibiotically active substance consisting of pradofloxacin or a salt or hydrate thereof, and a quaternary ammonium compound, wherein the waterbased formulation is a solution.

* * * * *